(12) United States Patent
Kanazawa et al.

(10) Patent No.: US 6,573,105 B1
(45) Date of Patent: Jun. 3, 2003

(54) TEST METHOD AND CONTROL METHOD FOR COATING LIQUID FOR ELECTROPHOTOGRAPHIC PHOTOCONDUCTOR

(75) Inventors: Tomoko Kanazawa, Kashihara (JP); Yoshihide Shimoda, Nara (JP); Sayaka Fujita, Kashihara (JP); Tadashi Nakamura, Nara (JP); Masayuki Sakamoto, Nabari (JP); Tatsuhiro Morita, Kashiba (JP)

(73) Assignee: Sharp Kabushiki Kaisha, Osaka (JP)

( * ) Notice: Subject to any disclaimer, the term of this patent is extended or adjusted under 35 U.S.C. 154(b) by 53 days.

(21) Appl. No.: 09/588,759

(22) Filed: Jun. 6, 2000

(30) Foreign Application Priority Data

Jun. 29, 1999 (JP) .............................................. 11-183650

(51) Int. Cl.$^7$ ......................... G01N 21/72; G01N 33/44; G01N 30/02
(52) U.S. Cl. ......................... 436/155; 436/147; 436/157; 436/161; 436/85
(58) Field of Search .................. 436/85, 147, 155, 436/157, 161; 430/83, 100, 143, 59, 96, 130

(56) References Cited

U.S. PATENT DOCUMENTS

| | | | | |
|---|---|---|---|---|
| 4,159,894 A | * | 7/1979 | Hu | 436/60 |
| 4,808,510 A | * | 2/1989 | Snow et al. | 430/287.1 |
| 5,128,229 A | * | 7/1992 | Katsukawa et al. | 430/83 |
| 5,364,731 A | * | 11/1994 | Shimizu | 430/143 |
| 5,437,952 A | * | 8/1995 | Hirai | 430/83 |
| 6,300,029 B1 | * | 10/2001 | Rokuthanzono | 430/100 |

FOREIGN PATENT DOCUMENTS

| | | |
|---|---|---|
| JP | Hei 3(1991)-17556 | 1/1991 |
| JP | Hei 4(1992)-67153 | 3/1992 |
| JP | Hei 10(1998)-48851 | 2/1998 |

OTHER PUBLICATIONS

Muguruma et al. "Surface–influence study for pyrofoil for Curie–point pyrolyzer upon the measurement of reproducibility on pyrogram", Bunseki Kagaku, Abstract, vol. 467, No. 7, Jul. 1998.*
Miller "Chromatography: concepts and contrasts", A Wiley–Interscience Publication, 1988, pp. 101–108.*

* cited by examiner

*Primary Examiner*—Jill Warden
*Assistant Examiner*—Yelena Gakh
(74) *Attorney, Agent, or Firm*—Nixon & Vanderhye P.C.

(57) ABSTRACT

A test method for a coating liquid for an electrophotographic photoconductor includes calculating a peak area ratio of a component to be analyzed in a coating liquid by pyrolysis gas chromatography, and comparing the peak area ratio with a pre-obtained peak area ratio of the component in a reference coating liquid having a known content of the component, to determine the ratio and/or content of the component in the coating liquid.

A control method for controlling a coating liquid based on the test result as obtained is also provided.

4 Claims, 2 Drawing Sheets

TEST METHOD AND CONTROL METHOD FOR COATING LIQUID FOR ELECTROPHOTOGRAPHIC PHOTOCONDUCTOR

CROSS-REFERENCE TO RELATED APPLICATION

This application is related to Japanese Patent Application No. HEI 11(1999)-183650 filed on Jun. 29, 1999,, whose priority is claimed under 35 USC §119, the disclosure of which is incorporated by reference in its entirety.

BACKGROUND OF THE INVENTION

1. Field of the Invention

The present invention relates to methods for testing and for controlling a coating liquid for an electrophotographic photoconductor, especially, an organic electrophotographic photoconductor, and a method of producing an electrophotographic photoconductor using the test and control methods.

2. Description of Related Art

Recently, in the fields of electrophotographic photoconductors (referred to just as "photoconductors" hereinafter) used in image forming apparatuses such as copying machines and laser printers, the development of organic photoconductive materials have made a remarkably progress and have become more widely in use than inorganic photoconductive materials which have been used. The photoconductors using organic photoconductive materials have some disadvantages in sensitivity, durability and stability to environment, but are much more advantageous than the inorganic photoconductive materials in toxicity, production costs, degree of freedom in material designing and the like. Now a variety of sensitizing methods are proposed.

Particularly, laminated photoconductors comprised of a charge generation layer and a charge transport layer exhibit an excellent sensitizing property and account for a majority of organic photoconductors currently in practical use. The laminated photoconductors are expected to be the mainstream photoconductors in the future.

In the laminated photoconductors, the charge generation layer contains a charge generation material which generates a charge carrier when irradiated with light, and the charge transport layer contains a charge transport material which receives and transports the charge carrier generated in the charge generation layer.

An undercoating layer is also provided on an electroconductive support with the intention of improving electrification characteristics, preventing unnecessary injection of charges from the electroconductive support, covering defects on the electroconductive support, preventing generation of pinholes, improvement adhesion of photoconductive layers (i.e., the electroconductive support and charge generation layer) and the like. Thus, the durability of photoconductors has been improved.

To produce a laminated photoconductor, organic photoconductive materials for constituting the respective photoconductive layers, together with binding resins, are dissolved or dispersed in organic solvents to prepare coating liquids for the photoconductor (referred to as "coating liquids" hereinafter), which are sequentially applied on an electroconductive support and dried.

Since these coating liquids are continuously used by being circulated in an apparatus for a long time or are used after being stored for a considerably long time, the composition and/or viscosity of the coating liquids often change due to natural vaporization of organic solvents. Such change is remarked particularly in the case where a mixed solvent of two or more solvents is used.

FIG. 3 illustrates an example of an apparatus for producing photoconductors, in which a coating liquid is circulated in a path formed by a coating vessel 6, an overflow liquid receiver 11, a recycling tube 12, an agitating vessel 7 provided with an agitator 13, a circulating pump 9, a filter 10, a circulating tube 8, and back to the coating vessel 6. The filter is provided for removing agglomerates of the coating liquid and dust generated in the apparatus. If the filter is used over a long time and the coating liquid contains a pigment dispersed as an organic photoconductive material, the filter catches agglomerates or gels of the pigment. As a result, the proportion of the pigment in the coating liquid changes.

Besides, the undercoating layer is often formed of a polyamide resin, and a hydrophilic organic solvent is used in consideration of the solubility of the polyamide resin. The hydrophilic organic solvent is easily mixed with water and it can hardly be grasped how much water has mixed in a coating liquid for the undercoating layer.

If a photoconductor is produced with use of a coating liquid whose composition has changed or has become ununiform and/or into which water has mixed, there possibly occur a decline in the film forming property of the coating liquid, defect in formed images and deterioration in electrophotograpic characteristics such as sensitivity. For example, if a photoconductor is produced with use of a coating liquid for the undercoating layer into which water has mixed and then the photoconductor is mounted in an image forming apparatus performing reverse development, small dark spots appear in white blank images.

Further, variation in the composition of the coating liquids among production lots may adversely affect characteristics of the photoconductors in the same manner as described above.

When the variation or ununiformity in composition, contamination of water or variation among production lots takes place in the coating liquids as described above, it is common to measure viscosity, clearness and particle distribution of the coating liquids and, according to the measurement results, add an insufficient component or judge that the coating liquids are out of use. In the apparatus of FIG. 3, the viscosity of the coating liquids is measured by a viscometer provided in the agitating vessel 7, and according to the measurement result, a solvent is added by an solvent supplementing device 16.

In addition to the measurement of the viscosity, some other means have been proposed for detecting change of the coating liquids with time.

For example, Japanese Unexamined Patent Publication No. HEI 10(1998)-48851 has disclosed a method of testing a coating liquid for a charge generation layer employing thermogravimetry for obtaining the proportion of a charge generation material to a binding resin, Japanese Unexamined Patent Publication No. HEI 3(1991)-17556 has disclosed a method of testing a photoconductor coating liquid employing a thin-layer chromatographic test method, and Japanese Unexamined Patent Publication No. HEI 4(1992)-67153 has disclosed a method of testing a photoconductor coating liquid employing absorption spectra by spectrophotometric analysis.

However, the above-mentioned method using the thermogravimetry requires a pre-treatment of evaporating an organic solvent in the coating liquid for the charge generation layer to dry and solidify the coating liquid, and in this pre-treatment, impurities may mix in the coating liquid. Moreover, since the organic solvent is removed by evaporation, the ratio of other components to the organic solvent cannot be obtained and the content of water cannot be quantitatively evaluated.

The method employing the thin-layer chromatographic test method can be used only for evaluating the dispersion state of a coating liquid containing a pigment. The method employing the absorption spectra can be used only for evaluating the dispersion state of a charge generation material.

SUMMARY OF THE INVENTION

Under these circumstances, an object of the present invention is to provide a test method for a coating liquid capable of effectively determining the ratio and/or content of a component to be analyzed in the coating liquid with good accuracy without contamination by impurities.

The present invention provides a test method for a coating liquid for a photoconductor comprising: calculating a peak area ratio of a component to be analyzed in a coating liquid by pyrolysis gas chromatography, and comparing the peak area ratio with a pre-calculated peak area ratio of the component in a reference coating liquid having a known content of the component, to determine the ratio and/or content of the component in the coating liquid.

The present invention also provides a control method for controlling a coating liquid for a photoconductor comprising: determining the ratio and/or content of a component to be analyzed in a coating liquid for a photoconductor by the above-described test method; and on the basis of the obtained result, adjusting the coating liquid so that its composition is constant or newly preparing the coating liquid, thereby to control the quality of the coating liquid.

The present invention further provides a production method of a photoconductor characterized by producing a photoconductor using a coating liquid therefor controlled by the above-described control method.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
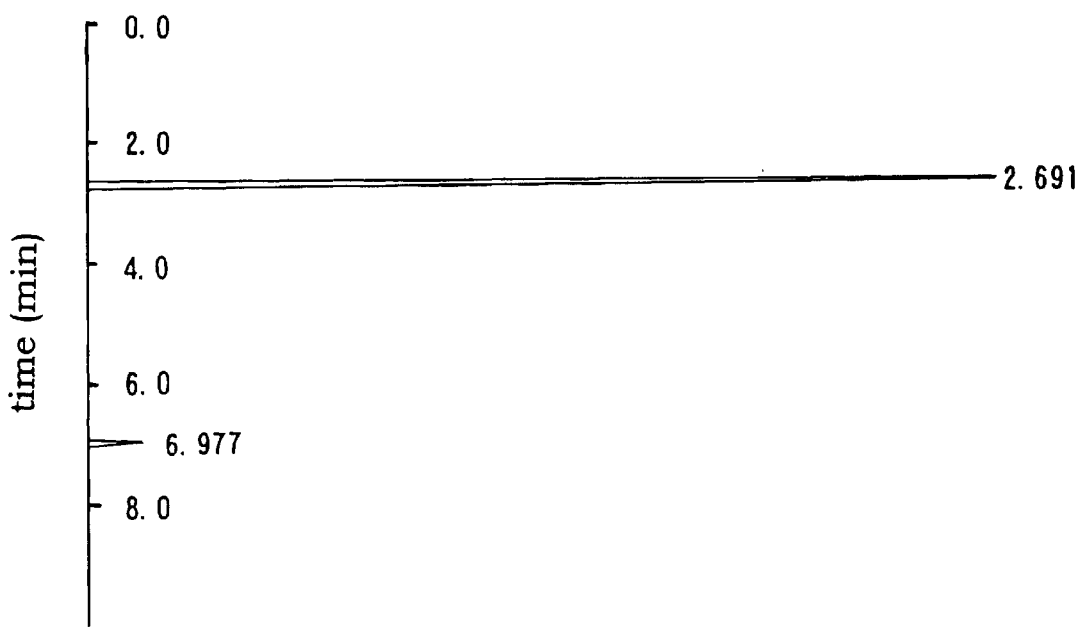
FIG. 1 is a chromatogram of an undercoating liquid using a mixed solvent of methanol and 1,2-dichoroethane by the test method of the present invention (Calibration Example 1)

The test method of the present invention serves to obtain the ratio and/or content of a component to be analyzed in a coating liquid effectively by use of pyrolysis gas chromatography.

Here the pyrolysis gas chromatography is a kind of gas chromatography with use of a pyrolyzer for pyrolyzing a sample. Pyrolysis may be performed by a filament, by a heating oven or by radioactive induction heating. The radioactive induction heating is preferred because it prevents a heat source from reacting with carbon or a halogen and does not disturb the flow of a carrier gas before and after a sample is introduced. However the pyrolysis is not limited to the radioactive induction heating.

Usually, if a coating liquid containing an organic or inorganic pigment is subjected to gas chromatography, the pigment adheres to a column and affects an apparatus adversely. For this reason, pre-treatment is needed. However, the use of the pyrolyzer enables a coating liquid containing a pigment to be introduced into gas chromatography without being pre-treated.

The test method of the present invention is now described step by step.

First, using a coating liquid containing components all in known contents, the following are determined beforehand: (1) if the coating liquid contains a pigment, the relationship between the ratio of the pigment and a resin and the ratio of the peak areas of the pigment and the resin in a pyrolysis gas chromatogram, (2) if the coating liquid contains two or more kinds of resins, the relationship between the ratio of the resins and the ratio of the peak areas of the resins in the pyrolysis gas chromatogram and/or (3) if the coating liquid contains two or more kinds of organic solvents, the relationship between the ratio of the organic solvents and the ratio of the peak areas of the organic solvents in the pyrolysis gas chromatogram.

Also a known amount of purified water is added to the coating liquid. The ratio of the added amount of purified water and an organic solvent and the relationship between the ratio and the peak area ratio of the purified water and the organic solvent in the pyrolysis gas chromatogram are determined beforehand.

The obtained results are plotted to produce a calibration for a component to be analyzed.

If a plurality of peaks are obtained with regard to one component by pyrolysis gas chromatography, the peak area ratio is preferably calculated from the highest peak of the plurality of peaks. The use of the highest peak allows accurate and quantitative handling of the component to be analyzed and consequently leads to a test with less errors.

Measurement by the pyrolysis gas chromatography is carried out as follows:

A given weight or volume of a coating liquid is dropped onto a pyrofoil selected from pyrofoils set at different temperatures according to the kind of a component to be analyzed. Subsequently, the pyrofoil is put into a pyrolyzer to sublime (vaporize) the coating liquid, which is then introduced to a gas chromatograph.

The peak area ratio of the component is calculated from the highest peak of the component obtained by a detector of pyrolysis gas chromatography and converted. The area ratio is compared with the pre-produced calibration to determine the ratio and/or content of the component to be analyzed.

The coating liquid to be tested by the test method of the present invention is not particularly limited so long as it is used for forming a photoconductor. Specifically, the coating liquid may be a coating liquid for an undercoating layer (referred to as an undercoating liquid), a charge generation layer, a charge transport layer and the like.

The characteristics of the laminated photoconductor are much affected by variation in the thickness and the composition of the photoconductive layers, especially the charge generation layer and the undercoating layer. The test method of the present invention is effectively applied for testing the coating liquids for these layers.

Particularly, the contamination of water into the undercoating layer increases small dark spots on white images onto the support of the photoconductor when reverse development is conducted (significantly in high-temperature, high-humidity ambience). Such small dark spots can be suppressed by testing and controlling the content of water in the undercoating liquid according to the test method of the present invention.

The kind of the undercoating liquid is not particularly limited so long as it is prepared by mixing a resin and an additive, if necessary, with a solvent.

As solvents, may be mentioned water and various organic solvents, especially, single solvents of methanol, ethanol, butanol, 1,3-dioxolane and a glycol; mixed solvents of water and alcohols; mixed solvents of two or more kinds of alcohols; chlorine-containing solvents such as dichloroethane, chloroform, trichloroethane, trichloroethylene and perchloroethylene; glycol solvents, and mixed solvents of 1,3-dioxolane and alcohols.

As resins used for the undercoating liquid, may be mentioned polyamides, copolymeric nylons, polyvinyl alcohols, polyurethanes, polyesters, epoxy resins, phenol resins, caseins, celluloses and gelatins, among which an alcohol-soluble copolymeric nylon is suitably used.

The additive may be added for the purpose of setting volume resistivity of the undercoating layer and improving aging characteristics during repeated use under a low-temperature and low-humidity environment. Examples thereof include inorganic pigments such as zinc oxide, titanium oxide, tin oxide, indium oxide, silica and antimony oxide.

The undercoating liquid is obtained by mixing the above mentioned solvent, resin and additive, followed by dissolving or dispersing. The inorganic pigment as the additive is dispersed in the coating liquid, and the addition ratio of the inorganic pigment to the resin is preferably 20/80 to 95/5 (by weight)

The coating liquid for the charge generation layer is not particularly limited so long as it contains, as a principle ingredient, a charge generation material which produces charges by irradiation of light, with which additives such as a plasticizer (e.g., an amine compound or a phenol compound) and a sensitizing agent (e.g., a diphenoquinone derivative and a benzoquinone derivative) may be mixed as required.

As charge generation materials, may be mentioned perylene pigments such as peryleneimide and perylenic anhydride; polycyclic quinone pigments such as quinacridone and anthraquinone; phthalocyanine pigments such as metallic or non-metallic phthalocyanines and halogenated non-metallic phthalocyanines; squarylium dyes; azulenium dyes; thiapyrylium dyes; azo pigments having a carbazole skeleton, styrylstilbene skeleton, triphenylamine skeleton, dibenzothiophene skeleton, oxadiazole skeleton, fluorenone skeleton, bisstilbene skeleton, distyryloxadiazole skeleton or distyrylcarbazole skeleton. Among them, non-metallic phthalocyanine pigments, oxotitanyl phthalocyanine pigments, biz-azo pigments having a fluorene ring and a fluorenone ring, biz-azo pigments and tris-azo pigments comprised of aromatic amines have a high charge generation property and can provide highly sensitive photoconductors. These charge generation materials may be used singly or as a combination of two or more kinds thereof.

The coating liquid for the charge transport layer is not particularly limited so long as it contains, as an indispensable ingredient, a charge transport material which receives and transfers the charges generated by the charge generation material and a binding resin, with which known additives such as a silicone leveling agent, an antioxidant, a plasticizer and a sensitizing agent may be mixed as required.

As charge transport materials, may be mentioned electron donor substances such as poly-N-vinyl carbazole and its derivatives, poly-γ-carbazolylethylglutamate and its derivatives, pyrene formaldehyde condensates and its derivatives, pyrene derivatives, polyvinyl phenanthrene, oxazole derivatives, oxodiazole derivatives, imidazole derivatives, 9-(p-diethylamino styryl)anthracene, 1,1-bis(4-dibenzylaminophenyl)propane, styryl anthracene, styryl pyrazoline, phenylhydrazones, hydrazone derivatives and azine compounds having a 3-methyl-2-benzothiazoline ring; electron acceptor substances such as fluorenone derivatives, dibenzothiophene derivatives, thiophene derivatives, phenanthrenequinone derivatives, pyridine derivatives, thioxanthone derivatives, benzo[c] cinnoline derivatives, phenazine oxide derivatives, tetracyanoethylene, tetracyanoquinodimethane, bromanil, chloranil and benzoquinone and the like. These charge transport materials may be used singly or as a combination of two or more kinds thereof. Where a charge transport material that has a film-forming property such as polyvinyl carbazole is used, the binding resin is not necessarily required.

As examples of binding resins usable for the coating liquids for the charge generation layer and the charge transport layer, may be mentioned photosetting resins such as styrene polymers, acrylic polymers, styrene-acrylic copolymers, polyethylene, ethylene-vinyl acetate copolymers, chlorinated polyethylene, olefin polymers (for example, polypropylene and ionomers), polyvinyl chloride, vinyl chloride-vinyl acetate copolymers, polyesters, alkyd resins, polyamides, polyurethanes, epoxy resins, polycarbonates, polyarylates, polysulfone, diallyl phthalate resins, silicone resins, ketone resins, polyvinyl butyral, polyethers, phenol resins, urethane acrylates and epoxy acrylates. These resins may be used singly or as a combination of two or more thereof. Among these resins, polystyrene, polycarbonates and polyarylates have a volume resistance of $10^{13}\Omega$ or more and are also excellent in the film-forming property and electrical characteristics.

As additives usable for the coating liquid for the charge transport layer, may be mentioned silicone leveling agents such as polysiloxane and antioxidants such as hydroquinone compounds, tocopherol compounds and phenol compounds.

Usually, a solvent is used in preparation of the coating liquids for the charge generation layer and the charge transport layer.

As examples of solvents, may be mentioned alcohols such as methanol, ethanol, isopropanol and butanol; aliphatic hydrocarbons such as n-hexane, octane and cyclohexane; aromatic hydrocarbons such as benzene, toluene and xylene; halogenated hydrocarbons such as dichloromethane, dichloroethane, carbon tetrachloride and chlorobenzene; ethers such as dimethyl ether, diethyl ether, tetrahydrofuran, 1,3-dioxolane, ethylene glycol dimethyl ether, ethylene glycol diethyl ether and diethylene glycol dimethyl ether; ketones such as acetone, methyl ethyl ketone and cyclohexanone; esters such as ethyl acetate and methyl acetate; dimethylformamide, dimethyl sulfoxide, which may be used singly or as a combination of two or more kinds thereof.

The charge generation material and the binding resin may be used in various ratios in the coating liquid for the charge generation layer. The charge generation material may be used in 5 to 1,000 parts by weight, preferably in 20 to 500 parts by weight, with respect to 100 parts by weight of the binding resin.

The charge transport material and the binding resins may be used in various ratios in the coating liquid for the charge transport layer so long as the transfer of charges is not inhibited. The charge transport material may be used in 10 to 500 parts by weight, preferably in 25 to 200 parts by weight, with respect to 100 parts by weight of the binding resin so that the charges generated in the charge generation layer by light irradiation can be easily transferred.

If the photoconductor is produced with use of a coating liquid containing a hydrophilic organic solvent (e.g., an alcohol solvent), it is very important to control the content of water (to grasp absorption or contamination of water) in the coating liquid for keeping constant the quality of the photoconductor.

The test method of the present invention can provide an accurate measurement of the content of water in the coating liquid, and therefore can be used for maintaining the quality of the coating liquid.

Also the method of the present invention can test the coating liquid not only for a change in a solvent due to natural vaporization but also for a change in the ratio of two or more solvents contained in a coating liquid which are different in vaporization.

Further, in addition to the ratio and/or content of the component in the coating liquid, the test method of the present invention can apply to quantitative measurement of impurities in the coating liquid.

The present invention provides a control method for controlling a coating liquid for a photoconductor comprising: determining the ratio and/or content of a component to be analyzed in a coating liquid for a photoconductor by the above-detailed test method; and on the basis of the obtained result, adjusting the coating liquid so that its composition is constant or newly preparing the coating liquid, thereby to control the quality of the coating liquid.

According to the control method, after the coating liquid is tested, a shortage of a solvent or the like is supplemented according as the need arises. Thus the coating liquid is maintained in a constant state by being returned to its initial state. Therefore, the life of the coating liquid can be increased. Or, if the test results show that the content of water in the coating liquid has risen up to such a level that the characteristics of the photoconductor are damaged, a new coating liquid may be prepared, though that depends on the kind of the coating liquid.

A combined use of viscosity measurement of the coating liquid with the test method of the present invention enables more accurate control of the coating liquid. In this case, on the basis of the test and measurement results, the coating liquid is so adjusted that its composition ratio and viscosity are constant or the coating liquid is newly prepared.

The present invention also provides a production method for a photoconductor characterized by producing a photoconductor using a coating liquid controlled by the above-detailed control method.

The undercoating layer, charge generation layer and charge transport layer of the photoconductor are formed by mixing the above-mentioned components for the respective layers by a known method, for example, by use of a roll mill, ball mill, attritor, paint shaker, sand mill or supersonic disperser to prepare the coating liquids and applying them by a known coating method, followed by drying.

The undercoating layer is formed by applying the undercoating liquid onto an electroconductive support, followed by drying. The undercoating layer is usually about 0.1 to 5 μm thick.

Here, the electroconductive support is not particularly limited to any kind so long as it is usually used as an electroconductive support of this kind. Examples thereof include a support of a metallic material such as aluminum and a support of plastic or paper provided with an electroconductive layer. The electroconductive support may be in the form of a drum, sheet, seamless belt or the like.

The charge generation layer is formed by applying the coating liquid therefor onto the undercoating layer, followed by drying. The charge generation layer is usually about 0.01 to 5 μm thick, preferably about 0.1 to 3 μm thick.

The charge transport layer is formed by applying the coating liquid therefor onto the charge generation layer, followed by drying. The charge generation layer is usually about 2 to 100 μm thick, preferably about to 30 μm thick.

In the laminated photoconductor, an undercoating layer and/or a barrier layer may be formed between the electroconductive support and the charge generation layer or the charge transport layer and between the charge generation layer and the charge transport layer, and a protective layer may be formed on the surface of the photoconductor, so long as they do not impede the characteristics of the photoconductor.

EXAMPLES

The present invention is now described in further detail with calibration examples and examples, which should not be construed to limit the scope of the invention. In the following description of examples, "part(s)" means "part(s) by weight" unless otherwise indicated.

Calibration Example 1

A mixed solvent was prepared from 50 parts of methanol and 50 parts of 1,2-dichloroethane. To this mixed solvent, 3 parts of titanium oxide and 3 parts of a copolymeric nylon resin (CM4000 produced by Toray Industries Inc., Japan) were admixed. The resulting mixture was dispersed by a paint shaker for 10 hours to give an undercoating liquid.

Undercoating liquids were also obtained in the same manner as described above except that the mixture ratio of methanol to 1,2-dichloroethane was varied to 10:90, 30:70, 70:30 and 90:10.

Methanol, 1 μl, was dropped in a pyrofoil at 150° C. by a syringe and subjected to high-frequency heating for 30 seconds in a pyrolyzer. Vaporized components obtained were introduced to a gas chromatograph. $N_2$ gas was circulated at a flow rate of 200 ml/min. as a carrier gas for gas chromatography, and the temperature of a column is set to 150° C.

The retention time of the maximum peak of methanol was detected by a detector through data conversion, and the retention time of the maximum peak of 1,2-dichloroethane was also detected in the same manner as described above.

The undercoating liquid having a methanol/1,2-dichloromethane mixture ratio of 50:50 was measured under the same conditions as described above to obtain peak areas at the retention times of methanol and 1,2-dichloromethane. The obtained results are shown in FIG. 1.

With regard to the undercoating liquids having the methanol/1,2-dichloromethane mixture ratios of 10:90, 30:70, 70:30 and 90:10, the peak areas at the retention times of methanol and 1,2-dichloromethane were obtained in the same manner.

Figure 2:
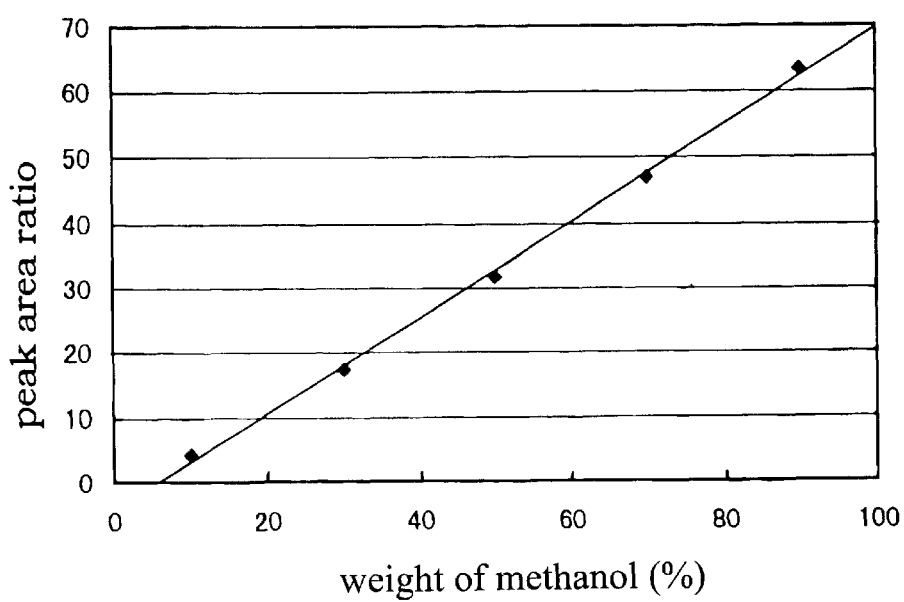
FIG. 2 is a calibration curve for a mixed solvent representing the relationship between the content of methanol (%) and a peak area ratio (%) of methanol with respect to 1,2-dichloroethane (Calibration Example 1)

A calibration curve was produced by plotting the relationship between the content (%) of methanol and a peak area ratio of methanol to 1,2-dichloroethane. The produced calibration curve is shown in FIG. 2.

Calibration Example 2.

A mixed solvent was prepared from 50 parts of methanol and 50 parts of 1,2-dichloroethane. To the mixed solvent, 3 parts of titanium oxide and 3 parts of a copolymeric nylon resin (CM4000 produced by Toray Industries Inc.) were admixed. The resulting mixture was dispersed by a paint shaker for hours to give an undercoating liquid.

Subsequently, undercoating liquids were also obtained in the same manner as described above except that 1%, 5%, 15% and 20% of purified water was added with respect to the total amount of the undercoating liquid.

The retention time of the maximum peak of water was detected under the same measurement conditions as in the calibration example 1.

The peak areas were obtained at the retention times with regard to the undercoating liquids to which 1%, 5%, 15% and 20% of purified water had been added.

A calibration curve was obtained by plotting the relationship of the added amount of purified water and the peak area ratio of water to methanol.

Calibration Example 3

A bis-azo pigment (chlorodianblue) represented by the following formula (1) and a butyral resin (produced by Union Carbide Corporation), each 1.5 part (mixture ratio of 50:50), were admixed to 97 parts of methylisoburylketone:

The resulting mixture was dispersed by a paint shaker for 10 hours to give a coating liquid for the charge generation layer.

Coating liquids for the charge generation layer were obtained in the same manner as described above except that the mixture ratio of the bis-azo pigment and the butyral resin is varied to 60:40, 70:30, 80:20 and 90:10.

About 5 μg of the bis-azo pigment was put in a pyrofoil at 650° C. and subjected to high-frequency heating for 30 seconds in a pyrolyzer. Vaporized components obtained were introduced to a gas chromatograph. $N_2$ gas was circulated at a flow rate of 250 ml/min. as a carrier gas for gas chromatography, and the temperature of a column is set to 230° C.

The retention time of the maximum peak of the bis-azo pigment was detected by a detector through data conversion, and the retention time of the maximum peak of the butyral resin was also detected in the same manner as described above.

The coating liquid for the charge generation layer having a bis-azo pigment/the butyral mixture ratio of 50:50, 2 μl, was dropped in a pyrofoil at 650° C. Measurement was conducted under the same conditions as described above, to obtain the peak areas at the retention times of the biz-azo pigment and the butyral resin.

The peak areas were obtained at the retention times of the bis-azo pigment and the butyral resin in the same manner with regard to the charge generation layer coating liquids having bis-azo pigment/butyral resin mixture ratios of 60:40, 70:30, 80:20 and 90:10.

A calibration curve was produced by plotting the relationship between the mixture ratio of the bis-azo pigment and the butyral resin and the peak area ratio of the butyral resin to the biz-azo resin.

Example 1

A mixed solvent was prepared from 50 parts of methanol and 50 parts of 1,2-dichloroethane. To this mixed solvent, 3 parts of titanium oxide and 3 parts of a copolymeric nylon resin (CM4000 produced by Toray Industries Inc.) were admixed. The resulting mixture was dispersed by a paint shaker for 10 hours to give an undercoating liquid.

The bis-azo pigment (chlorodianblue) represented by the formula (1) and the butyral resin (produced by Union Carbide Corporation), each 1.5 part (mixture ratio of 50:50), were admixed to 97 parts of methylisoburylketone. The resulting mixture was dispersed by a paint shaker for 10 hours to give a coating liquid for the charge generation layer.

A hydrazone compound (4-diethylaminobenzaldehyde-N, N-diphenylhydrazone), 1 part, and polycarbonate resin (lupilon produced by Mitsubishi Gas Chemical Company Inc., Japan), 1 part, was admixed to 8 parts of dichloromethane and further dissolved by stirring with a magnetic stirrer to give a coating liquid for the charge transport layer.

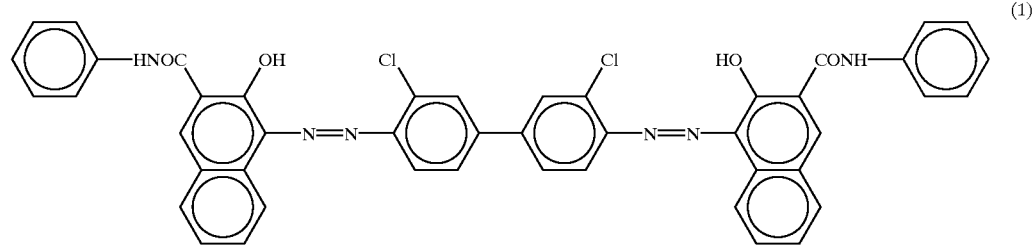

(1)

Figure 3:
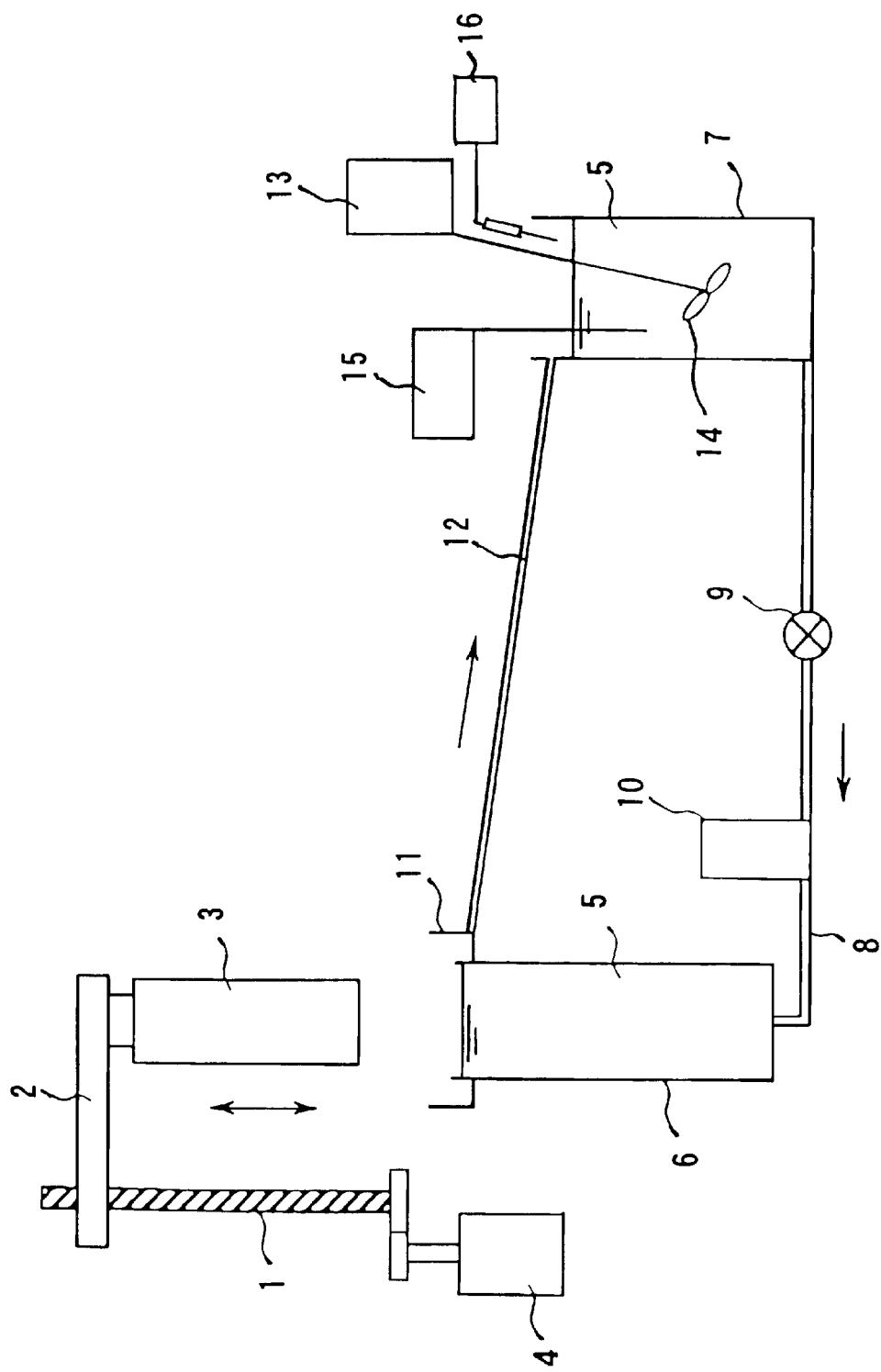
FIG. 3 is a schematic view of a known apparatus for producing photoconductors.

A cylindrical aluminum support (1 mm thickness×65 mm diameter×348 mm length) was used as a photoconductor support. The prepared undercoating liquid was applied onto the photoconductor support and dried by a known method using the apparatus shown in FIG. 3 to form an undercoating layer of 1.5 μm thickness. The prepared charge generation layer and charge transport layer coating liquids were sequentially applied onto the undercoating layer and dried in the same manner as the undercoating layer was formed, to give a charge generation layer of 0.8 μm thickness and a charge transport layer of 20 μm thickness. Thus a photoconductor was obtained.

A total of 500 photoconductors were prepared in the same manner and evaluated on a conforming article percentage (%) and the number of dark spots in white images. The obtained results are shown in Table 1—①.

The used undercoating liquid was measured under the same conditions as in Calibration Examples 1 and 2 for the peak areas at the retention times of methanol, 1,2-dichloroethan and water.

The obtained results are compared with the calibration curves produced in Calibration Examples 1 and 2 to obtain the mixture ratio of the solvents and the content of water.

The mixture ratio of methanol and 1,2-dichloroethane was 50:50 which did not shift from that when the coating liquid was prepared, and the content of water was 0.5%.

The viscosity of the used undercoating liquid measured 9.0 mPa·s.

Every one week after the photoconductor was first produced (hereinafter referred to as the "initial stage") the mixture ratio of methanol and 1,2-dichloroethane of the solvent in the undercoating liquid was determined and a shortage of the solvents was added so that the mixture ratio was maintained at 50:50 and the viscosity was maintained at 9.0 mPa·s.

The undercoating liquid after two months from the initial stage with the shortage of the solvents being added thereto was tested under the same conditions as in Calibration Example 2 to obtain the peak area at the retention time of water, which was then compared with the calibration curve produced in calibration Example 2 to give the content of water. The content of water was 2%.

A total of 500 photoconductors were prepared in the same manner as at the initial stage using the undercoating liquid to which the shortage of the solvents was added, and a charge generation layer coating liquid and a charge transport layer coating liquid which were prepared under the same conditions as at the initial stage. The photoconductors were evaluated on the conforming article percentage (%) and the number of dark spots in white images. The obtained results are shown in Table 1—②.

The undercoating liquid after two and a half months from the initial stage, with the shortage of the solvents being added thereto, was tested under the same conditions as in Calibration Example 2 to obtain the peak area at the retention time of water, which was then compared with the calibration curve produced in Calibration Example 2 to give the content of water. The content of water was 5%.

A total of 500 photoconductors were prepared in the same manner as at the initial stage using the undercoating liquid to which the shortage of the solvents was added, and a charge generation layer coating liquid and a charge transport layer coating liquid which were prepared under the same conditions as at the initial stage. The photoconductors were evaluated on the conforming article percentage (%) and the number of dark spots in white images. The obtained results are shown in Table 1—③.

The undercoating liquid after three months from the initial stage, with the shortage of the solvents being added thereto, was tested under the same conditions as in Calibration Example 2 to obtain the peak area at the retention time of water, which was then compared with the calibration curve produced in Calibration Example 2 to give the content of water. Since the content of water was 13%, this undercoating liquid was disposed of, and a new undercoating liquid was prepared under the same conditions as at the initial stage.

A total of 500 photoconductors were prepared in the same manner as at the initial stage using the newly prepared undercoating liquid, and a charge generation layer coating liquid and a charge transport layer coating liquid which were prepared under the same conditions as at the initial stage. The photoconductors were evaluated on the conforming article percentage (%) and the number of dark spots in white images. The obtained results are shown in Table 1—④.

The undercoating liquid controlled with use of viscosity measurement and pyrolysis gas chromatography as detailed above was found to be usable for about two and a half months.

Comparative Example 1

An undercoating liquid, a charge generation layer coating liquid and a charge transport layer coating liquid were prepared in the same manner as in Example 1, and applied and dried to obtain a photoconductor.

A total of 500 photoconductors are produced in the same manner and evaluated on the conforming article percentage (%) and the number of dark spots in white images. The obtained results are shown in Table 1—⑤.

The viscosity of the undercoating liquid, after use, measured 9.0 mPa·s.

Every one week after the initial stage, the viscosity of the used undercoating liquid was measured and the solvents were added thereto so that the viscosity was maintained at 9.0 mPa—s.

The undercoating liquid after two months from the initial stage, with the solvents being added thereto, was used together with a charge generation layer coating liquid and a charge transport layer coating liquid which were prepared under the same conditions as at the initial stage, to form a total of 500 photoconductors in the same manner as at the initial stage. The photoconductors were evaluated on the conforming article percentage (%) and the number of dark spots in white images. The obtained results are shown in Table 1—⑥.

The undercoating liquid after two and a half months from the initial stage, with the solvents being added thereto, was used together with a charge generation layer coating liquid and a charge transport layer coating liquid which were prepared under the same conditions as at the initial stage, to form a total of 500 photoconductors in the same manner as at the initial stage. The photoconductors were evaluated on the conforming article percentage (%) and the number of dark spots in white images. The obtained results are shown in Table 1—⑦.

The undercoating liquid after three months from the initial stage, with the solvent being added thereto, was used together with a charge generation layer coating liquid and a charge transport layer coating liquid which were prepared under the same conditions as at the initial stage, to form a total of 500 photoconductors in the same manner as at the initial stage. The photoconductors were evaluated on the conforming article percentage (%) and the number of dark spots in white images. The obtained results are shown in Table 1—⑧.

The undercoating liquid controlled with use only of the viscosity measurement as detailed above was found to be usable for substantially two and a half months, but the conforming article percentage declines significantly with time.

TABLE 1

|   |   | Time Period (months) | Conforming Article Ratio (%) | The Number of dark spots |
|---|---|---|---|---|
| ① | Ex. 1 | 0 | 98 | 10 |
| ② |  | 2 | 97 | 11 |
| ③ |  | 2.5 | 95 | 18 |
| ④ |  | 3 | 99 | 8 |
| ⑤ | Com. Ex. 1 | 0 | 99 | 9 |
| ⑥ |  | 2 | 90 | 11 |
| ⑦ |  | 2.5 | 86 | 21 |
| ⑧ |  | 3 | 68 | 52 |

The results of Example 1 and Comparative Example 1 show that the time period during which the undercoating liquid was usable was the same both in the case where the undercoating liquid was controlled using only the viscosity measurement and in the case where the undercoating liquid was controlled using the viscosity measurement and pyrolysis gas chromatographic test. However, concerning the conforming article percentage of photoconductors formed using the undercoating liquid, it was significantly better in the case where the undercoating liquid was controlled using the viscosity measurement and pyrolysis gas chromatographic test. Also, with regard to the number of dark spots, a little better results were observed with the undercoating liquid controlled using the viscosity measurement and pyrolysis gas chromatographic test.

The control with use only of the viscosity measurement of an undercoating liquid cannot provide the cause and degree of deterioration thereof, i.e., a shift in the mixture ratio of the solvents and the content of water, and therefore, with this control, it is impossible to judge before use whether or not the undercoating liquid can serve.

Example 2

An undercoating liquid, a charge generation layer coating liquid and a charge transport layer coating liquid were prepared in the same manner as in Example 1, and applied and dried to obtain a photoconductor.

A total of 500 photoconductors were produced in the same manner and evaluated on the conforming article percentage (%) and sensitivity (E*1/2($\mu$J/cm$^2$)). The obtained results are shown in Table 2—①.

The charge generation layer coating liquid after use was measured under the same conditions as in Calibration Example 3 to obtain the peak areas of the bis-azo pigment and the butyral resin at the retention time.

The obtained results were compared with the calibration curve produced in Calibration Example 3 to obtain the mixture ratio of the bis-azo pigment and the butyral resin.

The mixture ratio of the bis-azo pigment and the butyral resin was 50:50 which did not shift from that when the coating liquid was prepared.

The viscosity of the charge generation layer coating liquid measured 2.7 mPa·s.

Every one week after the initial stage, the mixture ratio of the bis-azo pigment and the butyral resin in the charge generation layer coating liquid was determined, and a shortage thereof was added so that was the mixture ratio of the bis-azo pigment and the butyral resin and the viscosity were maintained at 50:50 and 2.7 mPa·s, respectively. It is noted that the bis-azo pigment was added in the form of a dispersion in methylisobutylketone in which the particle diameter of the bis-azo pigment was the same as that at the initial stage.

When two months had passed since the initial stage while a shortage of the biz-azo pigment was added, the charge generation layer coating liquid was used to form a total of 500 photoconductors together with an undercoating liquid and a charge transport layer coating liquid which were prepared in the same manner as at the initial stage. The photoconductors were evaluated on the conforming article percentage and sensitivity (E*1/2). The obtained results are shown in Table 2—②.

When two and a half months had passed since the initial stage while a shortage of the biz-azo pigment was added, the charge generation layer coating liquid was used to form a total of 500 photoconductors together with an undercoating liquid and a charge transport layer coating liquid which were prepared in the same manner as at the initial stage. The photoconductors were evaluated on the conforming article percentage and sensitivity (E*1/2). The obtained results are shown in Table 2—③.

When three months had passed since the initial stage while a shortage of the biz-azo pigment was added, the charge generation layer coating liquid was used to form a total of 500 photoconductors together with an undercoating liquid and a charge transport layer coating liquid which were prepared in the same manner as at the initial stage. The photoconductors were evaluated on the conforming article percentage and sensitivity (E*1/2). The obtained results are shown in Table 2—④.

The charge generation layer coating liquid controlled with use of the viscosity measurement and pyrolysis gas chromatography test as detailed above was found to be usable for three months or more.

Comparative Example 2

An undercoating liquid, a charge generation layer coating liquid and a charge transport layer coating liquid were prepared in the same manner as in Example 2, and applied and dried to obtain a photoconductor.

A total of 500 photoconductors were produced in the same manner and evaluated on the conforming article percentage and sensitivity (E*1/2). The obtained results are shown in Table 2—⑤.

The viscosity of the charge generation layer coating liquid after use measured 2.7 mPa·s.

Every one week after the initial stage, the viscosity of the charge generation layer coating liquid was measured and methylisobutylketone was added so that the viscosity was maintained at 2.7 mPa·s.

When two months had passed since the initial stage while the solvent was added for adjustment, the charge generation layer coating liquid was used to form a total of 500 photoconductors together with an undercoating liquid and a charge transport layer coating liquid which were prepared in the same manner as at the initial stage. The photoconductors were evaluated on the conforming article percentage and sensitivity (E*1/2). The obtained results are shown in Table 2—⑦.

When two and a half months had passed since the initial stage while the solvent was added for adjustment, the charge generation layer coating liquid was used to form a total of 500 photoconductors together with an undercoating liquid and a charge transport layer coating liquid which were prepared in the same manner as at the initial stage. The photoconductors were evaluated on the conforming article percentage and sensitivity (E*1/2). The obtained results are shown in Table 2—⑦.

When three months had passed since the initial stage while the solvent was added for adjustment, the charge generation layer coating liquid was used to form a total of 500 photoconductors together with an undercoating liquid and a charge transport layer coating liquid which were prepared in the same manner as at the initial stage. The photoconductors were evaluated on the conforming article percentage and sensitivity (E*1/2). The obtained results are shown in Table 2—⑧.

The charge generation layer coating liquid controlled with use only of the viscosity measurement as detailed above was found to be usable for substantially two and a half months, but the conforming article percentage and sensitivity of the photoconductors decline significantly with time.

TABLE 2

| | | Time Period (months) | Conforming Article Ratio (%) | E* ½ (μJ/cm²) |
|---|---|---|---|---|
| ① | Ex. 2 | 0 | 97 | 0.204 |
| ② | | 2 | 98 | 0.208 |
| ③ | | 2.5 | 96 | 0.213 |
| ④ | | 3 | 96 | 0.214 |
| ⑤ | Com. Ex. 2 | 0 | 98 | 0.203 |
| ⑥ | | 2 | 92 | 0.215 |
| ⑦ | | 2.5 | 82 | 0.221 |
| ⑧ | | 3 | 63 | 0.301 |

The result of Example 2 and Comparative Example 2 show that the time period during which the charge generation layer coating liquid was usable was longer in the case where the charge generation layer coating liquid was controlled using the viscosity measurement and pyrolysis gas chromatographic test than in the case where the charge generation layer coating liquid was controlled using only the viscosity measurement. Also, concerning the conforming article percentage and sensitivity of photoconductors formed using the charge generation layer coating liquid, it was better in the case where the charge generation layer coating liquid was controlled using the viscosity measurement and pyrolysis gas chromatographic test.

The control of the coating liquid with use of both the viscosity measurement and the pyrolysis gas chromatography test can provide an accurate cause and degree of deterioration of the coating liquid, i.e., a shift in the mixture ratio of the biz-azo pigment and the butyral resin, and therefore, it is possible to take a countermeasure thereto in early stages.

In Examples 1 and 2, the undercoating liquid and charge generation layer coating liquid used for layered photoconductors were tested, but objects capable of being tested by the method of the invention are not limited thereto. The charge transport layer coating liquid can also be test.

According to the test method of the present invention, since the state of a coating liquid can be accurately grasped, it is possible to judge on the disposal of the coating liquid or to take measures such as the addition of a compensation liquid in early stages. Consequently, the life of coating liquid can be prolonged. Further, if a coating liquid gelates, it is possible to judge which causes the coating liquid to gelate, the shortage of a solvent or the contamination of water. Accordingly, photoconductors of excellent quality can be produced stably.

What is claimed is:

1. A test method for a coating liquid for an electrophotographic photoconductor, wherein the coating liquid is for an undercoating layer, a charge generation layer, or a charge transport layer of the photoconductor, the method comprising:

calculating a peak area ratio of at least first and second components in a coating liquid by pyrolysis gas chromatography, the first and second components being selected from at least one of: pigment, a resin, an organic solvent, and water, comparing the peak area ratio of the first and second components with a pre-calculated peak area ratio of the components in a reference coating liquid having a known content of the components, to determine the weight percentage of at least one of the components in the coating liquid, and wherein the pyrolysis gas chromatography used for calculating the peak area ratio of the first and second components comprises dropping a given weight or volume of the coating liquid onto a pyrofoil, wherein a temperature of the pyrofoil is determined by the component to be analyzed, and putting the pyrofoil into a pyrolyzer to vaporize the coating liquid which is then introduced to a gas chromatograph.

2. A test method for a coating liquid for an electrophotographic photoconductor, the method comprising:

calculating a peak area ratio of at least first and second components in a coating liquid by pyrolysis gas chromatography, the first and second components being selected from at least one of: pigment, a resin, an organic solvent, and water, comparing the peak area ratio of the first and second components with a precalculated peak area ratio of the components in a reference coating liquid having a known content of the components, to determine the weight percentage of at least one of the components in the coating liquid, and in the case where a plurality of peaks are obtained with regard to one component by the pyrolysis gas chromatography, the peak ratio is calculated from the highest peak, wherein the pyrolysis gas chromatography used for calculating the peak area ratio of the first and second components comprises dropping a given weight or volume of the coating liquid onto a pyrofoil, wherein a temperature of the pyrofoil is determined y the component to be analyzed, and putting the pyrofoil into a pyrolyzer to vaporize the coating liquid, which is then introduced to a gas chromatopraph.

3. A test method according to claim 1, wherein the coating liquid is a liquid for an image forming apparatus performing reverse development.

4. A test method according to claim 1, where the coating liquid contains one or more organic solvents which may absorb water or may vaporize, thereby causing change of a concentration of at least one of the components in the coating liquid.

* * * * *